United States Patent [19]
Nakano et al.

[11] Patent Number: 5,744,331
[45] Date of Patent: Apr. 28, 1998

[54] PROCESS FOR PRODUCING L-LEUCINE

[75] Inventors: Tetsuo Nakano, Machida; Masato Ikeda; Kuniki Kino, both of Hofu, all of Japan; Satoru Furukawa, Chesterfield, Mo.

[73] Assignee: Kyowa Hakko Kogyo Co., Ltd., Tokyo, Japan

[21] Appl. No.: 496,788

[22] Filed: Jun. 29, 1995

[30] Foreign Application Priority Data

Jun. 30, 1994 [JP] Japan ................................. 6-149679

[51] Int. Cl.$^6$ ....................................... C12P 13/06
[52] U.S. Cl. ................ 435/116; 435/252.33; 435/252.8; 435/849
[58] Field of Search ................. 435/116, 252.8, 435/252.33, 849

[56] References Cited

U.S. PATENT DOCUMENTS 3,865,690  2/1975  Okumura et al. .
4,421,854  12/1983  Updike et al. .

FOREIGN PATENT DOCUMENTS 0530803  3/1993  European Pat. Off. .
50-125086  10/1975  Japan .
56-72695  6/1981  Japan .

OTHER PUBLICATIONS

Fed. Proc. 33 (5 Part 2) 1974; Conference Abstr. 960 Quay et al "Leucing Transport in Azaleucing Resistant Mutants of *E. coli*".

Database WPI, Derwent Publications Ltd. London, GB; AN 81-46747D & JP-A-56 051 989 (Ajinomoto KK), 9 May 1981.

Database WPI, Derwent Publications Ltd. London, GB; AN 84-117429 & JP-A-59 055 194 (Nippon Kayaku KK) 30 Mar. 1984.

Database WPI, Derwent Publications Ltd. London, GB; AN 81-56158D & JP-A-56 072 695 (Ajinomoto KK) 16 Jun. 1981.

*Primary Examiner*—Herbert J. Lilling
*Attorney, Agent, or Firm*—Antonelli, Terry, Stout & Kraus, LLP

[57] ABSTRACT

Disclosed is a process for producing L-leucine which comprises culturing in a medium a microorganism belonging to the genus Escherichia and having resistance to a leucine analogue and an ability to produce L-leucine, allowing L-leucine to accumulate in the culture, recovering L-leucine therefrom.

6 Claims, No Drawings

PROCESS FOR PRODUCING L-LEUCINE

BACKGROUND OF THE INVENTION

The present invention relates to a process for producing L-leucine by fermentation. L-leucine is an amino acid which plays nutritiously important role for humans and animals and is used for medicine, foods, additives to feed, etc.

To produce L-leucine by direct fermentation, there is known a process by using microorganisms belonging to the genus Escherichia, Serratia, Corynebacterium or Arthrobacter. With respect to the process for producing L-leucine by culturing microorganisms belonging to the genus Escherichia, for example, known is a process by culturing microorganisms belonging to the genus Escherichia which are resistant to β-2-thienylalanine (Japanese Published Unexamined Patent Application No. 72695/81).

With regard to the process for producing L-leucine by culturing microorganisms having resistance to a leucine analogue, known is a process by culturing a microorganism belonging to the genus Salmonella (Science 156, 1107 (1967)), Arthrobacter (JP-A-125086/75 and JP-A-220697/83), Corynebacterium or Brevibacterium (U.S. Pat. No. 3,865,690).

An efficient process for producing L-leucine is always in demand from an industrial viewpoint.

SUMMARY OF THE INVENTION

According to the present invention, there is provided a process for producing L-leucine, comprising culturing in a medium a microorganism belonging to the genus Escherichia and having resistance to a leucine analogue and an ability to produce L-leucine, allowing L-leucine to accumulate in the culture and recovering L-leucine therefrom.

DETAILED DESCRIPTION OF THE INVENTION

In the present invention, any microorganism can be used so long as it belongs to the genus Escherichia, and has resistance to a leucine analogue and has the ability to produce L-leucine.

The leucine analogue to be used in the present invention includes 4-azaleucine, 5,5,5-trifluoroleucine, etc.

The suitable microorganisms used in the present invention can be obtained by subjecting L-leucine-producing-microorganisms belonging to the genus Escherichia to conventional mutagenesis such as treatment with N-methyl-N'-nitro-N-nitrosoguanidine and X-ray irradiation, spreading the resulting microorganisms on a minimum agar plate medium containing a leucine analogue, and picking up colonies which grow on the minimum agar plate medium.

Alternatively, the suitable microorganisms can be obtained by subjecting a mutant having resistance to a leucine analogue derived from a wild strain to mutagenesis for endowment of L-leucine productivity.

Further, the suitable microorganisms can be obtained by endowing, with resistance to a leucine analogue, L-valine-producing microorganisms belonging to the genus Escherichia by the above mutagenesis. As the L-valine-producing microorganism of *Escherichia coli*, mention is made of *Escherichia coli* H-9068.

The preferred example of the suitable microorganisms to be used in the present invention includes *Escherichia coli* H-9070 having resistance to 4-azaleucine and *Escherichia coli* H-9072 having resistance to 5,5,5-trifluoroleucine.

According to the present invention, production of L-leucine can be carried out by culturing suitable microorganisms in a conventional manner. As the medium, any of synthetic and natural media may be used so long as it appropriately contains carbon sources, nitrogen sources, inorganic substances and a trace amount of other nutrients which the used strain requires.

As the carbon sources, carbohydrates such as glucose, fructose, lactose, molasses, cellulose hydrolyzate, hydrolyzate of crude sugar and starch hydrolyzate; and organic acids such as pyruvic acid, acetic acid, fumaric acid, malic acid and lactic acid can be used. Further, glycerol, alcohols such as ethanol, etc. can also be used provided that they can be assimilated by the strain used.

As the nitrogen sources, ammonia; various inorganic or organic ammonium salts such as ammonium chloride, ammonium sulfate, ammonium acetate and ammonium phosphate; amines, peptone, meat broth, corn steep liquor, casein hydrolyzate, bean-cake hydrolyzate, various cultured cells and their digested products, etc. can be used.

As the inorganic substances, potassium dihydrogenphosphate, dipotassium hydrogenphosphate, magnesium phosphate, magnesium sulfate, sodium chloride, ferrous sulfate, manganese sulfate, copper sulfate, calcium carbonate, etc. can be used.

Culturing is carried out under aerobic conditions, e.g. by shaking culture and agitation culture with aeration, at the incubation temperature of 20° to 40° C., preferably 28° to 37° C. The pH of the medium is maintained in the range of 5 to 9 preferably, at around neutrality. The pH is adjusted with calcium carbonate, inorganic or organic acids, alkaline solution, ammonia, pH buffers agents, or the like.

Usually, after culturing for 1 to 7 days, L-leucine is accumulated in the culture.

After the completion of culturing, precipitates such as cells are removed from the culture by means of centrifugation, etc. and L-leucine can be recovered from the supernatant by using ion exchange treatment, concentration, salting-out, etc. in combination.

Certain embodiments of the invention are illustrated in the following examples.

EXAMPLE 1

Preparation of a mutant having resistance to 4-azaleucine or 5,5,5-trifluoroleucine A protrophic strain, *Escherichia coli* H-9068 derived spontaneously from a methionine- and diaminopimeric acid-requiring strain, *Escherichia coli* ATCC 21530 by reverse mutation was subjected to a conventional mutation treatment with N-methyl-N'-nitro-N-nitrosoguanidine (0.5 mg/ml, 33° C., 30 minutes), and then spread on a minimum agar plate medium (0.5% glucose, 0.2% ammonium chloride, 0.3% potassium dihydrogenphosphate, 0.6% disodium phosphate, 0.01% magnesium sulfate, 20 mg/l calcium chloride, 2% agar, pH 7.2) containing one g/l of 4-azaleucine. After culturing at 33° C. for 2 to 5 days, the large colonies which grew on the medium were picked up as the mutant strain having resistance to 4-azaleucine and subjected to L-leucine production test to select strains having L-leucine-producing ability greater than that of the parent strain at a frequency of about 10%. Among these mutants, the strain having the highest production of L-leucine was designated as *Escherichia coli* H-9070.

Strain H-9070 was deposited on Jun. 21, 1994 with National Institute of Bioscience and Human-Technology Agency of Industrial Science and Technology, Japan under the Budapest Treaty with accession number FERM BP-4704.

The above-mentioned process was repeated, except that 0.3 g/l of 5,5,5-trifluoroleucine was used in place of one g/l of 4-azaleucine, and the large colonies were picked up as the mutant strains having resistance to 5,5,5-trifluoroleucine. Among these mutants, strains having L-leucine-producing ability greater than that of the parent strain were obtained at a frequency of about 10%. Among these mutants, the strain having the highest production of L-leucine was designated as *Escherichia coli* H-9072.

Strain H-9072 was deposited on Jun. 21, 1994 with National Institute of Bioscience and Human-Technology Agency of Industrial Science and Technology, Japan under the Budapest Treaty with accession number FERM BP-4706.

The mutant strains were compared with the parent strain in degree of resistance to 4-azaleucine or 5,5,5-trifluoroleucine in the following manner.

The mutant strains and the parent strain were each cultured on a natural agar plate medium (1% tripton, 0.5% yeast extract, 1% sodium chloride, 2% agar pH 7.2) for 24 hours. The cultured cells were suspended in sterilized water, and the cell suspension was spread to give a density of about $1 \times 10^3$ cells/cm$^2$ on the above-mentioned minimum agar plate medium containing 4-azaleucine or 5,5,5-trifluoroleucine in amounts shown in Tables 1 and 2. Culturing was carried out at 33° C. for 72 hours, and the degree of the growth was observed. The degree of resistance to 4-azaleucine or 5,5,5-trifluoroleucine was expressed in terms of degree of growth. The results are shown in Tables 1 and 2. H-9070 and H-9072 strains have higher degree of resistance to 4-azaleucine and 5,5,5-trifluoroleucine, respectively, than that of the parent H-9068 strain.

TABLE 1

| | Amount of 4-Azaleucine (g/l) | | |
|---|---|---|---|
| Strain | 0 | 0.5 | 1.0 |
| H-9068 | + | − | − |
| H-9070 | + | + | + |

+: sufficient growth
−: no growth

TABLE 2

| | Amount of 5,5,5-Trifluoroleucine (g/l) | | |
|---|---|---|---|
| Strain | 0 | 0.1 | 0.3 |
| H-9068 | + | − | − |
| H-9072 | + | + | + |

+: sufficient growth
−: no growth

EXAMPLE 2

L-Leucine production test:

*Escherichia coli* H-9070 and *Escherichia coli* H-9072 obtained in Example 1 and the parent strain *Escherichia coli* H-9068 were inoculated into 20 ml of a seed medium (2% glucose, 1% peptone, 1% yeast extract, 0.25% sodium chloride, pH 7.0) in a 300-ml Erlenmeyer flask, and cultured with shaking at 30° C. for 16 hours. The resulting seed culture (2 ml) was inoculated into 250 ml of a fermentation medium (6% glucose, 0.2% corn steep liquor, 1.6% ammonium sulfate, 0.1% potassium dihydrogenphosphate, 4% magnesium phosphate, 1% calcium carbonate, pH 7.0) in a 2-liter Erlenmeyer flask, and cultured with shaking at 30° C. for 72 hours.

After the completion of culturing, the amount of L-leucine accumulated was determined by high performance liquid chromatography.

The results are shown in Table 3.

TABLE 3

| Strain | Amount of L-leucine (g/l) |
|---|---|
| H-9068 | 0.0 |
| H-9070 | 3.4 |
| H-9072 | 3.9 |

One liter of each fermentation broth obtained by culturing strains H-9070 and H-9072 was centrifuged at 3000 rpm for 10 minutes to remove the cells and other impurities therefrom. Each of the thus-obtained supernatants was passed through a column packed with a strongly acidic cation exchange resin, DIAION (type H$^+$; product of Mitsubishi Chemical Corporation, Japan) to absorb L-leucine thereon. The column was washed with water and subjected to elution with 0.5N aqueous ammonia to collect the L-leucine fractions. The collected fractions were concentrated and ethanol was added to the concentrate. By storing the mixture under cooling, 2.6 g and 3.0 g of L-leucine crystals having a purity of 98% or higher were obtained from the fermentation broth of strains H-9070 and H-9072, respectively.

What is claimed is:

1. A process for producing L-leucine which comprises culturing in a medium a microorganism belonging to the genus Escherichia in the culture, and recovering L-leucine therefrom, wherein the microorganism has resistance to a leucine analogue and which produces at least 3.4 g/l L-leucine, and is derived from an L-valine-producing strain.

2. The process according to claim 1, wherein the leucine analogue is 4-azaleucine or 5,5,5-trifluoroleucine.

3. The process according to claim 1, wherein said microorganism belongs to the species *Escherichia coli*.

4. The process according to claim 1, wherein said L-valine producing microorganism is *Escherichia coli* H-9068.

5. A process for producing L-leucine which comprises culturing in a suitable medium a microorganism selected from *Escherichia coli* H-9070 deposited as FERM BP-4704 and *Escherichia coli* H-9072 deposited as FERM BP-4706, and recovering L-leucine therefrom.

6. A process for producing L-leucine which comprises culturing in a suitable medium a microorganism belonging to the genus Escherichia in the culture, and recovering L-leucine therefrom, wherein the microorganism has resistance to a leucine analogue and an ability to produce L-leucine, and is derived from an L-valine-producing strain; wherein the L-valine producing strain is *E. Coli* H-9068 deposited as ATCC 21530.

* * * * *